(12) United States Patent
Bruna et al.

(10) Patent No.: US 6,488,964 B2
(45) Date of Patent: Dec. 3, 2002

(54) PROCESS FOR MANUFACTURING COATED GABAPENTIN OR PREGABALIN PARTICLES

(75) Inventors: Etienne Bruna, Jouy (FR); Edouard Gendrot, Garnay (FR); Charles Chauveau, Valbonne (FR); Alain-Gilles Demichelis, Grasse (FR)

(73) Assignee: Societe Laboratoires des Products Ethiques - Ethypharm, Houdan (FR)

( * ) Notice: Subject to any disclaimer, the term of this patent is extended or adjusted under 35 U.S.C. 154(b) by 0 days.

(21) Appl. No.: 09/777,490

(22) Filed: Feb. 5, 2001

(65) Prior Publication Data

US 2002/0012679 A1 Jan. 31, 2002

Related U.S. Application Data

(63) Continuation of application No. PCT/FR99/01811, filed on Jul. 23, 1999.

(30) Foreign Application Priority Data

Aug. 3, 1998 (FR) .............................. 98/10091

(51) Int. Cl.⁷ .............................. A61K 9/16; A61K 9/14; A61K 9/20; A61K 31/195
(52) U.S. Cl. ..................... 424/490; 424/489; 424/464; 424/465; 424/494; 514/561
(58) Field of Search ................. 424/489, 490, 424/464, 465, 494; 514/561

(56) References Cited

U.S. PATENT DOCUMENTS 4,024,175 A    5/1977   Satzinger et al. ........... 260/468
5,464,632 A  * 11/1995  Cousin et al.

FOREIGN PATENT DOCUMENTS

| EP | 0237506 | 9/1987 | ............ A61K/9/16 |
| EP | 0458751 A1 | 11/1991 | ......... A61K/31/195 |
| EP | 0523847 | 4/1996 | ............ A61K/9/00 |
| GB | 2157170 A | 10/1985 | ............ A61K/9/22 |
| WO | 9603122 A2 | 2/1996 | ......... A61K/31/195 |

* cited by examiner

*Primary Examiner*—Thurman K. Page
*Assistant Examiner*—Amy E Pulliam
(74) *Attorney, Agent, or Firm*—Heslin Rothenberg Farley & Mesiti P.C.

(57) ABSTRACT

A process for manufacturing coated particles of γ-aminobutyric acid analogue, whose lactam content by weight relative to the weight of γ-aminobutyric acid analogue is less than 0.5% is disclosed. The process is characterized in that a coating solution of at least one polymer in an organic solvent is sprayed onto the particles of γ-aminobutyric acid analogue.

16 Claims, No Drawings

PROCESS FOR MANUFACTURING COATED GABAPENTIN OR PREGABALIN PARTICLES

CROSS REFERENCE TO RELATED APPLICATIONS

This application is a continuation of PCT application PCT/FR99/01811, filed Jul. 23, 1999, and published in French as WO 00/07568 on Feb. 17, 2000. PCT/FR99/01811 claimed the priority of French application FR98/10091, filed Aug. 3, 1998. The entire disclosures of both are incorporated herein by reference.

FIELD OF THE INVENTION

The invention relates to a process for manufacturing coated particles of γ-aminobutyric acid (GABA) analogue containing less than 0.5% of lactam by weight relative to the weight of GABA analogue.

The invention also relates to the coated particles which can be obtained by the said process, as well as to any pharmaceutical form using the said coated particles.

BACKGROUND

In the description hereinbelow and in the claims, the invention is described more particularly in relation to the γ-aminobutyric acid analogues chosen from the group comprising gabapentin and pregabalin. However, as already stated, the process applies to any γ-aminobutyric acid analogue which can produce lactam molecules as degradation product.

Gabapentin, also known as 1-aminomethylcyclohexaneacetic acid, is a γ-aminobutyric acid (GABA) analogue. It has anti-convulsant properties and is used in the treatment of epilepsy. This well-known molecule is described in particular in documents U.S. Pat. No. 4,024,175 and U.S. Pat. No. 4,087,544.

From the point of view of pharmacokinetics, it is essential for the concentration of gabapentin in the plasma to reach its peak in 2 to 3 hours.

This is one of the reasons why gabapentin is currently sold in France in the form of gel-capsules filled with a mixture of powder consisting of gabapentin, hydrated lactose, corn starch and talc. The gel-capsules contain 100 mg, 300 mg or 400 mg doses of active principle and are sold under the trade name NEURONTIN® by Parke-Davis.

Although gel-capsules allow the satisfactory concentration of gabapentin in the plasma to be obtained, they are, however, unsuitable for pediatric use.

To solve this problem, attempts have been made to present gabapentin in the form of an aqueous solution.

However, the document Pharmaceutical Research, Volume 9, Number 5, 1992, demonstrates:
  on the one hand, that gabapentin is liable to be degraded in aqueous solution to give, by intramolecular cyclization, a lactam-type degradation product, the content of which should not exceed 0.5% by weight relative to the weight of the active principle for any pharmaceutical form, irrespective of the dosage;
  and, on the other hand, that gabapentin has a sufficiently bitter taste for it to be essential to mask its taste.

To solve the problem of masking the taste, document EP-A-0,458,751 proposed presenting gabapentin in the form of particles coated with a hydrophilic first layer of a water-insoluble polymer and a hydrophobic second layer. Even though satisfactory masking of the taste is obtained, the process of coating the first layer requires the presence of water, such that an intramolecular cyclization of gabapentin can be expected, leading to the formation of lactam inside the finished product itself.

Pregabalin is also a γ-aminobutyric acid analogue which is known as an anti-epileptic agent and is more particularly described in document WO 98/58641 for its application as an anti-inflammatory agent. The Applicant has observed that pregabalin displayed a phenomenon identical to that of gabapentin as regards its degradation in aqueous solution into lactam molecules. In addition, just like gabapentin, pregabalin must reach a maximum concentration in the plasma in 2 to 3 hours. Finally, this molecule also has a bitter taste, making it difficult to use in its native form in a pharmaceutical formulation.

SUMMARY OF THE INVENTION

The first problem which the invention proposes to solve is to provide a pharmaceutical form of a GABA analogue, whose lactam content is less than 0.5% by weight relative to the weight of GABA analogue.

The second problem which the invention proposes to solve is to provide a pharmaceutical form of a GABA analogue which can be used in paediatrics.

The third problem which the invention proposes to solve is to provide a pharmaceutical form of a GABA analogue in which the bitter taste of the said analogue is masked, while at the same time giving a maximum concentration in the plasma in 2 to 3 hours.

To do this, the invention proposes a process for manufacturing coated particles of a γ-aminobutyric acid analogue whose lactam content by weight relative to the weight of GABA analogue is less than 0.5%.

This process is characterized in that a coating solution comprising at least one polymer in at least one organic solvent is sprayed on to the said particles of γ-aminobutyric acid analogue.

In a first embodiment, the γ-aminobutyric acid analogue is gabapentin.

In another embodiment of the invention, the γ-aminobutyric acid analogue is pregabalin.

It has been found, entirely surprisingly, that the fact of coating the gabapentin or the pregabalin particles with a polymer dissolved in an organic solvent makes it possible to obtain a lactam content in the coated particle of less than 0.5% by weight relative to the weight of gabapentin or of pregabalin. In addition, the polymer coating also makes it possible to mask the taste of the γ-aminobutyric acid analogue without, however, delaying its release, thus making it possible to obtain usual concentrations in the plasma.

DETAILED DESCRIPTION OF THE INVENTION

To obtain the masking of the taste while at the same time allowing the rapid release of the gabapentin, the polymer represents between 60 and 80% by weight of the gabapentin.

For a polymer proportion of less than 60%, sufficient masking of the taste is not obtained. Conversely, for a polymer proportion of greater than 80%, the gabapentin taste is entirely masked, but the active principle may not be released quickly enough.

Advantageously, the gabapentin particles are coated to a proportion of 70% by weight of polymer.

Similarly, as regards pregabalin, to obtain masking of the taste while at the same time allowing rapid release of the molecule, the polymer represents between 15 and 30% by weight of the pregabalin.

For a polymer proportion of less than 15%, sufficient masking of the taste is not obtained. Conversely, for a polymer proportion of greater than 35%, the gabapentin taste is entirely masked, but the active principle may not be released quickly enough.

Advantageously, the pregabalin particles are coated to a proportion of 20% by weight of polymer.

Moreover, the various processes for manufacturing gabapentin or pregabalin give particles which can range between 2 micrometers and a few millimeters in size.

If the size of the particles of active principle analogue is too small, i.e. about 50 micrometers, spraying of the solution leads to non-uniform coating of the particles.

To solve this problem, it is sought to increase the size of the particles by spraying a solution of a water-soluble binder in an organic solvent on to the said particles by the so-called fluidized air bed technique, also known as "spray coating", after which the aggregated particles obtained are screened and calibrated.

The actual coating of the gabapentin or pregabalin is carried out on the aggregated or non-aggregated particles, the size of which is between 100 and 400 micrometers, preferably in the region of 250 micrometers, by the same so-called fluidized bed technique.

The coated gabapentin or pregabalin particle obtained is in the form of a coated, aggregated or non-aggregated particle, the size of which is between 100 and 450 micrometers, with a median of about 250 micrometers.

To dissolve the polymer, the organic solvent is chosen from the group comprising acetone, ethanol and isopropanol, alone or as a mixture.

According to one advantageous embodiment, the polymer is dissolved in a solvent comprising 50 parts of acetone and 50 parts of ethanol per 100 parts on a mass/mass basis.

Similarly, when a step of pre-uniforming of the size of the gabapentin or pregabalin particles is carried out, the binder is dissolved in an organic solvent which is identical to or different from the one used in the spraying operation.

Moreover, to obtain a polymer coating which both allows the γ-aminobutyric acid analogue to be released rapidly and allows the taste of the active molecule to be masked, the polymer is chosen from the group comprising polymethacrylate, aminoethyl methacrylate copolymers and cellulose polymers, alone or as a mixture.

Advantageously, the polymethacrylate is a Eudragit, in particular Eudragit E® sold by the company Röhm.

Among the cellulose polymers which can be chosen are ethyl cellulose, hydroxypropylmethyl cellulose, hydroxypropyl cellulose, and cellulose acetophthalate, alone or as a mixture. Moreover, it may be necessary to combine plasticizers such as ethyl phthalate with the said polymer.

To optimize the masking of the taste of the active principle, the coating solution can also contain a sweetener chosen from the group comprising aspartam, potassium acesulfam, sodium saccharinate, monoammonium glycyrrhizinate, sugars and derivatives, as well as polyols and derivatives, alone or as a mixture.

In practice, the sweetener represents between 1 and 6% by weight of the γ-aminobutyric acid analogue.

Moreover, to avoid electrostatic phenomena during the coating operation and thereby allow better control of the process, the solution also comprises an antistatic agent chosen from the group comprising colloidal silica, precipitated silica and talc.

In practice, the antistatic agent represents between 2 and 8% by weight of the γ-aminobutyric acid analogue, advantageously between 5 and 6% by weight.

According to another characteristic of the process of the invention, the spraying both of the dissolved polymer and of the dissolved binder is carried out as already stated by the fluidized bed technique.

On the laboratory scale, the spraying-air inlet temperature should be minimal and more particularly between 35 and 45° C., advantageously 40° C.

On the industrial scale, the spraying-air inlet temperature is higher and is more particularly between 40 and 80° C., advantageously 60° C.

Be that as it may, and in both cases, the temperature of the aggregated or non-aggregated particles during the coating operation should be minimal and advantageously between 20 and 30° C.

The coated gabapentin or pregabalin particles obtained can be used in any adequate pharmaceutical form, it being understood that the lactam content of the said pharmaceutical form is less than 0.5% by weight relative to the weight of GABA analogue.

In a first embodiment, the coated particles are used in their native form, in the form of a sachet.

According to one advantageous embodiment of the invention, the coated particles can be subjected to a tabletting step after the said coated particles have been dry-premixed with the usual tabletting excipients.

The excipients used for the manufacture of these tablets are known to those skilled in the art and are chosen in particular from the group comprising diluents, lubricants, flavourings and sweeteners, alone or as a mixture.

The tablets which can be obtained according to the process of the invention may advantageously be of two types.

The first type corresponds to multiparticulate tablets which break down quickly without water being supplied, in less than 60 seconds in the oral cavity, these tablets also being known as Flashtab®, which is a trademark registered by the Applicant, and are described more particularly in document EP-A-548,356.

In this case, the excipients added during the tabletting step also comprise at least one disintegrating agent capable of allowing rapid crumbling of the active principle.

Advantageously, the disintegrating agent is chosen from the group comprising sodium carboxymethylcellulose, crosslinked PVP (also known as cross-povidone) and carboxymethyl starch.

Moreover, the polymer intended for coating the gabapentin or pregabalin particles must be chosen such that it is insoluble at neutral pH, corresponding to the pH of the saliva (thus masking the taste) and such that it is soluble or permeable at a pH of between 1 and 4 corresponding to the gastric pH.

Furthermore, the hardness of the tablet is between 30 and 70 N, advantageously 50 N.

The second type of tablet corresponds to so-called "fast-dispersible" tablets, i.e. tablets which are rapidly dispersible in water, which can be broken down in a very short time <1 minute, preferably <15 seconds, in a minimum volume of water which will depend on the mass of the tablet.

The latter pharmaceutical form can thus advantageously be used in paediatrics.

In this case, the excipients added during the tabletting operation will also comprise not only a crumbling agent but also an agent for maintaining the coated particles in suspension or a swelling agent.

Furthermore, the hardness of the tablet obtained is between 30 and 100 N, advantageously 70 N.

The invention and the advantages ensuing therefrom will emerge better from the preparation examples which follow.

Since the examples are all carried out on the laboratory scale, various parameters are adjusted accordingly.

In the three examples which follow, measurement of the lactam content is performed by quantitative determination carried out by HPLC relative to an external lactam standard.

EXAMPLE 1

1—Manufacture of coated gabapentin particles a) Manufacture of agglomerated particles Gabapentin particles are first aggregated using the following mixture:

| Gabapentin | 400 mg |
|---|---|
| PVP K30 (binder) | 20 mg |
| Ethanol QSP | 180 mg |

PVP=polyvinyl providone sold by BASF

In accordance with the process of the invention, the size of the active principle particles is made uniform by spraying the binder dissolved in ethanol on to the gabapentin particles by the spray-coating technique. The fluidization air temperature is adjusted to 40° C., the temperature of the particles during manufacture being 21° C.

The aggregated particles obtained are subsequently screened and then calibrated in order to obtain a majority of particles between 250 and 350 microns in size.

b) Coating of the aggregated particles

The aggregated particles thus formed are then coated according to the same process by spraying with a solution comprising:

| Eudragit E 100 | 280 mg |
|---|---|
| Ethanol QSP | 1027 mg |
| Acetone QSP | 1027 mg |
| Colloidal silica | 42 mg |

1: Aerosil R972 sold by Degussa c) Percentage of lactam produced at the end of manufacture of coated particles The percentage of lactam by weight relative to the weight of the gabapentin present in the coated particles ranges between 0.07 and 0.1% from one batch to the other.

2—Manufacture of Fast-dispersible Gabapentin Tablets

Once the gabapentin particles have been coated, the said particles are mixed with the powder mixture comprising:

| Diluent | mannitol[1] | 206.7 |
|---|---|---|
| Swelling agent | microcrystalline cellulose[2] | 190.8 |
| Disintegrating agent | cross-povidone[3] | 116.6 |
| Lubricant | PEG-6000 | 15.9 |

[1]Pearlitol: sold by Roquette
[2]Avicel CE 15: sold by FMC
[3]Kollidon CL sold by BASF 1: Pearlitol: sold by Roquette 2: Avicel CE 15: sold by FMC 3: Kollidon CL sold by BASF The tablets are prepared on a rotary tabletter equipped with a punch 18 mm in diameter. The pressure exerted is 16±2 KNewton.

The hardness of the tablets obtained is about 70 Newtons.

a) Dissolution tests

Tests of dissolution of the tablets obtained were carried out in acidic medium (0.06 N HCl) under the standard conditions (apparatus 2, and paddle speed of 50 rotations per minute).

The tests were carried out under conditions of storing the tablets at 25° C. and 60% relative humidity.

The results are given in the table below.

| Storage conditions | Dissolution in 5 minutes | | Dissolution in 10 minutes | | Dissolution in 15 minutes | | Dissolution in 20 minutes | |
|---|---|---|---|---|---|---|---|---|
| | Average (%) | spread from the average (%) | average (%) | spread from the average (%) | average (%) | spread from the average (%) | average (%) | spread from the average (%) |
| 25° C./60% RH After storage for 3 Months | 97 | 87–102 | 102 | 99–104 | 103 | 100–106 | 102 | 100–105 |

As the above table shows, 96% of the tablet is dissolved in 5 minutes, which proves the capacity of the polymer to release the active principle quickly.

b) Percentage of lactam contained in the fast-dispersible tablet

The percentage of lactam present in the tablet at the end of manufacture ($T_0$), after 42 days, 3 and 6 months storage was moreover measured. The results are given in the table below (percentage of lactam by weight relative to the weight of gabapentin).

| Storage conditions | Storage time | % lactam |
|---|---|---|
| | time zero | 0.10 |
| 25° C./60% RH | 3 months | 0.13 |
| 25° C./60% RH | 6 months | 0.14 |
| 30° C./60% RH | 6 months | 0.16 |
| 40° C./75% RH | 3 months | 0.21 |
| 40° C./75% RH | 6 months | 0.29 |

It is observed that the tablet is stable with respect to the degradation product for six months under accelerated storage conditions.

As already stated, this type of tablet has the advantage of being able to be used in paediatrics.

EXAMPLE 2

1/ Manufacture of coated gabapentin particles a) The same manufacturing process as that described in Example 1 is followed, starting with a mass of gabapentin equal to 300 mg, the other constituents being used on a pro rata basis.

b) The percentage of lactam assayed in the coated particles at the end of the process ranges between 0.07 and 0.10% by weight relative to the weight of gabapentin from one batch to another.

2/ Manufacture of the fast-dispersible tablet

Fast-dispersible gabapentin tablets containing a 300 mg dose are then manufactured by mixing together the coated particles obtained and the following powdered mixture:

| | |
|---|---|
| Pearlitol 400 DC (diluent) | 155 mg |
| Avicel CE 15 (swelling agent) | 143 mg |
| Kollidon CL (disintegrating agent) | 87.5 mg |
| PEG 6000 (lubricant) | 11.9 mg |

The tablets are manufactured on a rotary tabletter equipped with a punch 16 mm in diameter. The pressure exerted is 12±2 KN. The hardness of the tablet obtained is about 55 N.

a) Dissolution test

As previously, the percentages of dissolution of gabapentin in acidic medium were then calculated. The results are given in the table below.

| Storage conditions (After storage for 3 months) | Dissolution in 5 minutes | | Dissolution in 10 minutes | | Dissolution in 15 minutes | | Dissolution in 20 minutes | |
|---|---|---|---|---|---|---|---|---|
| | average (%) | spread from the average (%) | average (%) | Spread from the average (%) | average (%) | spread from the average (%) | average (%) | spread from the average (%) |
| 25° C./60% RH | 99 | 94–101 | 102 | 98–105 | 102 | 100–105 | 102 | 99–104 |
| 40° C./75% RH | 98 | 94–101 | 99 | 95–104 | 98 | 94–102 | 99 | 96–103 | b) Percentage of lactam

The percentage of lactam present in the tablet obtained according to the invention was also measured. The results are given in the table below (on a weight basis relative to the weight of gabapentin).

| Storage conditions | Storage time | % lactam |
|---|---|---|
|  | zero point | 0.10 |
| 25° C./60% RH | 3 months | 0.14 |
| 25° C./60% RH | 6 months | 0.25 |
| 30° C./60% RH | 6 months | 0.18 |
| 40° C./75% RH | 3 months | 0.23 |
| 40° C./75% RH | 3 months | 0.23 |
| 40° C./75% RH | 6 months | 0.32 |

EXAMPLE 3

1/ Manufacture of coated pregabalin particles

In this step, coated pregabalin particles having the composition below are prepared:

| Pregabalin | 150 mg |
|---|---|
| Eudragit E 100 | 45 mg |
| Potassium acesulfam | 7.9 mg |
| Talc | 10.9 mg |

The coated particles are manufactured according to the process of the invention in a fluidized bed by spraying with a solution comprising Eudragit, potassium acesulfam and talc in 96% ethanol.

This fluidized bed technique is performed in apparatus of the Glatt/GPGC 1 type, the temperature of the product being between 20 and 25° C.

The percentage of lactam measured on the coated pregabalin particles is:

| Storage conditions | Storage time | % lactam |
|---|---|---|
|  | zero point | <0.01 |
| 25° C./60% RH | 1 month | <0.01 |
| 25° C./60% RH | 2 months | <0.01 |
| 30° C./60% RH | zero point | <0.01 |
| 40° C./75% RH | zero point | <0.01 |
| 40° C./75% RH | 1 month | <0.01 |
| 40° C./75% RH | 2 months | <0.01 |

2/ Manufacture of the fast-crumbling multiparticulate tablet

Once the pregabalin particles have been coated, the said particles are mixed with a powder mixture comprising:

| Mannitol (diluent) | 474.2 mg |
|---|---|
| Cross-povidone (disintegrating agent) | 80 mg |
| Monoammonium glycyrrhizinate (sweetener) | 14 mg |
| Flavouring | 10 mg |
| Magnesium stearate | 8 mg |

The hardness of the tablets obtained is 40 N.

a) Dissolution test

The percentages of dissolution of pregabalin in acidic medium were calculated under the same conditions as in Examples 1 and 2. The results are given in the table below.

| Dissolution in 5 minutes | Dissolution in 10 minutes | Dissolution in 20 minutes | Dissolution in 60 minutes |
|---|---|---|---|
| 100.5 | 102.4 | 101.5 | 101.9 | b) Percentage of lactam

The percentage of lactam calculated on the tablets is represented in the table below.

| Storage conditions | Storage time | % lactam |
|---|---|---|
|  | zero point | <0.01 |
| 25° C./60% RH | 1 month | <0.01 |
| 25° C./60% RH | 2 months | <0.01 |
| 30° C./60% RH | zero point | <0.01 |
| 40° C./75% RH | zero point | <0.01 |
| 40° C./75% RH | 1 month | 0.023 |
| 40° C./75% RH | 2 months | 0.029 |

The advantages of the invention emerge clearly from the description. It is noted in particular that the invention simultaneously allows the three problems to be solved, namely:

to provide a pharmaceutical form of GABA analogue whose percentage of toxic lactam is less than 0.5%;

to mask the bitter taste of the γ-aminobutyric acid analogues;

and to obtain a maximum concentration of the active molecule in the plasma in 2 to 3 hours after ingestion.

The coated particles also have the advantage, besides their conventional manufacturing process, of being able to be incorporated in particular into Flashtab® or fast-dispersible type tablets, these being tablets which are not swallowed directly, but rather after having been broken down on contact with saliva in the mouth in the first case, or on contact with water in the second case.

It is thus no longer necessary in this case to ingest solid forms, which can prove to be inadequate, in particular in children and the elderly, and complicated in the case of treating a person suffering from epilepsy.

As already stated, the invention is not limited to a process for manufacturing coated gabapentin or pregabalin particles, but rather relates to any γ-aminobutyric acid analogue liable to degrade into lactam molecules in aqueous solution.

What is claimed is:

1. Process for manufacturing coated particles of pregabalin, whose lactam content by weight relative to the weight of pregabalin is less than 0.5% characterized in that a coating solution comprising between 15 and 30% by weight of a polymer chosen from the group consisting of polymethacrylate, aminoethyl methacrylate copolymers and cellulose polymers, alone or as a mixture, in at least one organic solvent is sprayed on to the said particles of pregabalin.

2. Process according to claim 1, wherein the particles of pregabalin are made uniform in size before hand, by spraying a solution of a water-soluble binder in an organic solvent on to the said particles, followed by screening and calibration of the aggregated particles obtained.

3. Process according to claim 1, wherein the coating solution is sprayed on in a fluidized bed.

4. Process according to claim 1, wherein the organic solvent is chosen from the group comprising acetone, ethanol and isopropanol, alone or as a mixture.

5. Process according to claim 4, characterized in that the organic solvent comprises 50 parts of acetone and 50 parts of ethanol per 100 parts on a mass/mass basis.

6. Process according to claim 2, characterized in that the binder is dissolved in ethanol.

7. Process according to claim 1, wherein the coating solution also contains a sweetener chosen from the group consisting of aspartame, potassium acesulfam, monoammonium glycyrrhizinate, sodium saccharinate, sugars and derivatives, and polyols and derivatives, alone or as a mixture.

8. Process according to claim 1, wherein the coating solution also contains an antistatic agent chosen from the group consisting of colloidal silica, precipitated silica and talc.

9. Process according to claim 1, wherein the coated particles obtained are dry-mixed with tabletting excipients before subjecting them to a tabletting step in order to obtain tablets.

10. Process according to claim 9, characterized in that the tabletting excipients are chosen from the group consisting of diluents, lubricants, flavourings and sweeteners, alone or as a mixture.

11. Process according to claim 10, characterized in that the tabletting excipients also comprise at least one disintegrating agent chosen from the group consisting of sodium carboxymethylcellulose, cross-povidone and carboxymethyl starch.

12. Process according to claim 11, characterized in that the tabletting excipients also comprise an agent for maintaining the coated particles in suspension.

13. Coated particles obtained by the process according to claim 1.

14. Tablet obtained by the process according to claim 1.

15. Multiparticulate tablet obtained by the process of claim 11 for oral administration without the use of water, said tablet disintegrating in less than 60 seconds in the oral cavity.

16. Fast-dispersible multiparticulate tablet obtained by the process of claim 12.

* * * * *